United States Patent
Anand et al.

(10) Patent No.: US 8,400,147 B2
(45) Date of Patent: Mar. 19, 2013

(54) PREDICTING PROPERTIES OF LIVE OILS FROM NMR MEASUREMENTS

(75) Inventors: Vivek Anand, Houston, TX (US); Robert Freedman, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 517 days.

(21) Appl. No.: 12/765,096

(22) Filed: Apr. 22, 2010

(65) Prior Publication Data

US 2010/0271019 A1    Oct. 28, 2010

Related U.S. Application Data

(60) Provisional application No. 61/171,588, filed on Apr. 22, 2009.

(51) Int. Cl.
*G01V 3/00* (2006.01)
(52) U.S. Cl. ........................................ 324/303; 324/306
(58) Field of Classification Search .................. 324/303, 324/306, 307, 309
See application file for complete search history.

(56) References Cited

U.S. PATENT DOCUMENTS

| 7,091,719 | B2 | 8/2006 | Freedman |
| 7,309,983 | B2 | 12/2007 | Freedman |
| 7,683,613 | B2 * | 3/2010 | Freedman et al. ............ 324/306 |
| 7,924,001 | B2 * | 4/2011 | Cao Minh ..................... 324/303 |
| 8,013,601 | B2 * | 9/2011 | Cheng et al. .................. 324/303 |

OTHER PUBLICATIONS

Freedman, R., "New Approach for Solving Inverse Problems Encountered in Well-Logging and Geophysical Applications," Petrophysics Vol. 47, No. 2, pp. 93-111 (Apr. 2006).
A. Vivek & R. Freedman, "New Methods for Predicting Properties of Live Oils From NMR," SPWLA 50th Annual Logging Symposium, Jun. 21-24, 2009.

\* cited by examiner

*Primary Examiner* — Louis Arana
(74) *Attorney, Agent, or Firm* — Darla P. Fonseca

(57) ABSTRACT

A fluid property of live crude oil removed from an earth formation is determined using nuclear magnetic resonance (NMR) measurements. A pressure cell, located on or near the earth's surface, and in which the live crude oil is disposed, is provided. An NMR tool capable of making NMR measurements on the live crude oil is provided, as is a database linking existing NMR data and the fluid property. A mapping function is created from a combination of radial basis functions and parameters of the mapping function are derived using the database. NMR data are acquired on the live crude oil using the NMR tool, and the fluid property is estimated from the acquired NMR data using the mapping function.

20 Claims, 11 Drawing Sheets

PREDICTING PROPERTIES OF LIVE OILS FROM NMR MEASUREMENTS

CROSS-REFERENCE TO RELATED APPLICATIONS

This application claims priority to and the benefit of U.S. Provisional Patent Application No. 61/171,588, filed Apr. 22, 2009.

BACKGROUND OF THE DISCLOSURE

Nuclear Magnetic Resonance (NMR) tools used for well-logging or downhole fluid characterization measure the response of nuclear spins in formation fluids to applied magnetic fields. Downhole NMR tools typically have a permanent magnet that produces a static magnetic field at a desired test location (e.g., where the fluid is located). The static magnetic field produces a non-equilibrium magnetization in the fluid. The magnetization is aligned along the direction of the static field. The magnitude of the induced magnetization is proportional to the magnitude of the static field. The proportionality constant is the static magnetic susceptibility. A transmitter antenna produces a time-dependent radio frequency magnetic field that is perpendicular to the direction of the static field. The NMR resonance condition is satisfied when the radio frequency is equal to the Larmor frequency, which is proportional to the magnitude of the static magnetic field. The radio frequency magnetic field produces a torque on the magnetization vector that causes it to rotate about the axis of the applied radio frequency field. The rotation results in the magnetization vector developing a component perpendicular to the direction of the static magnetic field. This causes the magnetization vector to precess around the static field at the Larmor frequency. At resonance between the Larmor and transmitter frequencies, the magnetization is tipped to the transverse plane (i.e., a plane normal to static magnetic field vector). A series of radio frequency pulses are applied to generate spin echoes that are measured with the antenna.

Crude oil properties such as viscosity, molecular composition, gas-oil ratio, and SARA fractions are crucial parameters for evaluating, for example, reservoir quality, producibility, and compartmentalization. In the past decade, physical and empirical model-based equations have been developed which relate the properties of crude oils to Nuclear Magnetic Resonance (NMR) measurements. However, in general, the existing models are too simplistic to accurately estimate crude oil properties. This limitation arises because of the inherent complexity of crude oils. That is, they are mixtures of hydrocarbon and non-hydrocarbon molecules of varying shapes, sizes, and concentrations. There are also shortcomings in other database approaches such as, for example, Artificial Neural Networks (ANN). Implementation of ANN requires computationally expensive and lengthy iterative training that may not converge to a solution.

Characterization of reservoir fluids is crucial for several aspects of reservoir development and management. For example, fluid properties such as viscosity and molecular composition are used to calculate flow rates and sweep efficiencies of secondary and tertiary recoveries. Gas-oil ratio (GOR) of reservoir fluids is an important parameter for material selection of well completion and design of surface facilities. Asphaltene and wax concentrations are key considerations for flow assurance in completions, pipelines, and surface facilities. Estimation of fluid properties at different depths in a reservoir provides indications of compositional grading and compartmentalization within the reservoir. The direct measurement of fluid properties in a laboratory, however, is time consuming and expensive. As a result, it is useful to estimate fluid properties from measurements such as NMR which can be performed with relative ease and at downhole temperature and pressure conditions.

NMR response of fluids provides a link between microscopic molecular motions and macroscopic properties such as viscosity and composition. The relationship between viscosity and relaxation time of pure fluids was established by the phenomenological relaxation theory of Bloembergen, Purcell, and Pound (BPP). Brown studied proton relaxation in a suite of crude oils with various compositions and viscosities. The viscosities of the samples varied from about 0.5 to 400 cp. He found that the relaxation times showed an inverse dependence on viscosity over the entire range. Since the early work of Brown, several physical and empirical models have been proposed that relate crude oil properties to NMR response. However, the predictive power of these models is limited for several reasons. First, crude oils are complex mixtures of linear, branched, cyclic, and aromatic hydrocarbons. They also contain compounds with sulfur, oxygen, and nitrogen atoms, in addition to small concentrations of metallic impurities such as nickel and vanadium. As a result, the NMR response of crude oils is governed by a multitude of intra- and inter-molecular interactions between the constituents. It is difficult to accurately describe all such interactions by simple physical or empirical models. Second, the detailed information contained in the shapes of $T_1$ or $T_2$ distributions is not accounted for in the models. Last, the empirical constants involved in the models are not universal, and may differ by as much as a factor of two for different oils.

Radial basis functions (RBFs) are used for several applications in numerical and scientific computing, such as solution of partial differential equations, artificial neural networks, surface reconstruction, computer-aided-design, computer graphics, and multivariate interpolation. A unique property of RBFs is that they provide excellent interpolants for high dimensionality data sets of poorly distributed data points. This property follows from the mathematical result that a linear system of interpolation equations with RBFs is invertible under very mild conditions. The theoretical background for the invertibility of the RBF interpolation matrix has been established and a study evaluating 29 interpolating methods concluded that interpolation by multiquadric RBFs outperformed most methods. The application of RBFs for numerical solution of elliptic, hyperbolic, and parabolic differential equations has been developed and RBFs have been extensively used to approximate scattered, non-uniformly distributed data.

The traditional approach to solve an inverse problem involves fitting a theoretical or empirical model to the measurements. This approach is not generally suited to petrophysical systems because they are too complex to be parameterized by forward models. For example, the complex molecular interactions that govern NMR relaxation of crude oils can not be fully described by simple forward models. A technique using RBFs to solve complex inverse problems for which accurate forward models are unknown has been previously introduced, demonstrated, and used, inter alia, to predict viscosities and molecular compositions of dead oils from NMR measurements.

SUMMARY

A fluid property of live crude oil removed from an earth formation is determined using nuclear magnetic resonance (NMR) measurements. A pressure cell, located on or near the earth's surface, and in which the live crude oil is disposed, is provided. An NMR tool capable of making NMR measurements on the live crude oil is provided, as is a database linking existing NMR data and the fluid property. A mapping function is created from a combination of radial basis functions and parameters of the mapping function are derived using the database. NMR data are acquired on the live crude oil using the NMR tool, and the fluid property is estimated from the acquired NMR data using the mapping function.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
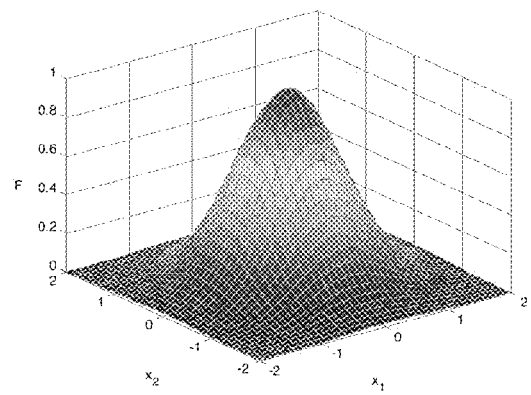
FIG. 1 is a plot of a Gaussian RBF in two dimensions ($x_1$, $x_2$) centered at the origin.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

NMR measurements can be used in a model-independent method to make quantitative predictions of live oil properties. This method assumes the physics connecting the NMR data to the oil properties is implicitly contained within a laboratory database of NMR and pressure-volume-temperature (PVT) measurements performed on a representative suite of live oils. In one embodiment, the input measurements (such as $T_2$ distributions) are mapped to live oil properties (such as viscosities or molecular compositions) using an interpolating function that is a linear combination of Gaussian radial basis functions. The parameters of the interpolating function are calibrated using the database. The interpolating function with calibrated parameters can be used to estimate properties of live oils that are not in the database.

Let us assume there exists a database which comprises crude oil properties and NMR measurements at corresponding temperature and pressure conditions. The oil properties and NMR measurements are hereby referred to as database outputs and inputs, respectively. The estimation technique proposes that the underlying physical relationship between database outputs and inputs can be approximated by a mapping function which is a linear combination of Gaussian RBFs. The coefficients of the mapping function are calibrated using the database. The mathematical properties of Gaussian RBFs ensure that the mapping function is unique. The mapping function can be visualized as a multivariate interpolation between database inputs and outputs. For a sample not included in the database, the mapping function can be employed to estimate the required output using only the input measurement. The mathematical formulation of the method is described below.

The notation in this section follows the notation in the paper, Freedman, R., 2006, New Approach for Solving Inverse Problems Encountered in Well-Logging and Geophysical Applications, *Petrophysics*, vol. 47, p. 93-111.

Let $\vec{f}(\vec{x})$, $\vec{x} \in \mathbb{R}^n$ and $\vec{f} \in \mathbb{R}^m$ be a real-valued vector function of n variables, and let values of $\vec{f}$ be given at N distinct points, $\vec{x}_i$. The interpolation problem is to construct the function $\vec{F}(\vec{x})$ that approximates $\vec{f}(\vec{x})$ and satisfies the interpolation equations:

$$\vec{F}(\vec{x}_i) = \vec{y}_i, i=1, 2 \ldots N \tag{1}$$

The interpolation function is constructed as a linear combination of nonlinear functions such as RBFs, given as:

$$\vec{F}(\vec{x_i}) = \sum_{i=1}^{N} \vec{c_i} \varphi(\|\vec{x} - \vec{x_i}\|), \quad (2)$$

$$i = 1, 2 \ldots N.$$

The functions $\phi(\|\vec{x}-\vec{x_i}\|) \in [0, \infty)$ are called "radial" because the argument of the function depends only on the distance between, not the direction of, $\vec{x_i}$ and an arbitrary input vector at which the function is to be evaluated. The argument is given by the Euclidean norm in n-dimensional hyperspace, i.e., $$\|\vec{x} - \vec{x_i}\| = \sqrt{\sum_{j=1}^{n} (x_j - x_{i,j})^2} \quad (3)$$

The forms of commonly used RBFs are listed in Table 1.
Table 1: Forms of commonly used RBFs
$\phi(r) = r$ linear
$\phi(r) = r^2 \log(r)$ thin-plate spline
$\phi(r) = \exp(-\beta r^2)$ Gaussian
$\phi(r) = (r^2 + \gamma^2)^{1/2}$ multiquadrics The real valued coefficients $\vec{c}$ of the interpolating function in Eq. (2) can be obtained by requiring that the interpolation equations are satisfied exactly. Thus, Eqs. (1) and (2) imply that the coefficients can be obtained by solving the following linear system of equations:

$$\Phi \cdot C = Y \quad (4)$$

where C is a matrix whose rows consist of the coefficient vectors, i.e., $$C = \begin{bmatrix} c_{1,1} & c_{1,2} & \cdots & c_{1,m} \\ c_{2,1} & c_{2,2} & \cdots & c_{2,m} \\ \vdots & \vdots & \vdots & \vdots \\ c_{N,1} & c_{N,2} & \cdots & c_{N,m} \end{bmatrix}. \quad (5)$$

The matrices $\Phi$ and Y are N×N and N×m matrices, respectively. They contain the RBF and database vectors and are given by:

$$\Phi = \begin{bmatrix} \varphi_{1,1} & \varphi_{1,2} & \cdots & \varphi_{1,N} \\ \varphi_{2,1} & \varphi_{2,2} & \cdots & \varphi_{2,N} \\ \vdots & \vdots & \vdots & \vdots \\ \varphi_{N,1} & \varphi_{N,2} & \cdots & \varphi_{N,N} \end{bmatrix}, \quad (6)$$

$$Y = \begin{bmatrix} y_{1,1} & y_{1,2} & \cdots & y_{1,m} \\ y_{2,1} & y_{2,2} & \cdots & y_{2,m} \\ \vdots & \vdots & \vdots & \vdots \\ y_{N,1} & y_{N,2} & \cdots & y_{N,m} \end{bmatrix}. \quad (7)$$

It can be mathematically proved that matrix $\Phi$ is non-singular for certain functional forms of RBFs such as Gaussian and multiquadrics. This property ensures that the mapping function of Eq. (2) is unique. Hence, using a database with N samples, a mapping function that is consistent with the measurements can be uniquely constructed using Eqs. (2) and (4). For an unknown sample not included in the database, the desired output $\vec{y}$ can be obtained by evaluating the mapping function at the corresponding input $\vec{x}$, i.e., $$\vec{y} = \vec{F}(\vec{x}) \quad (8)$$

One of the most commonly used RBFs is the normalized Gaussian RBF, given as:

$$\varphi(\|\vec{x} - \vec{x_i}\|) = \frac{\exp\left(-\frac{\|\vec{x} - \vec{x_i}\|^2}{2s_i^2}\right)}{\sum_{j=1}^{N} \exp\left(-\frac{\|\vec{x} - \vec{x_j}\|^2}{2s_j^2}\right)}. \quad (9)$$

The normalization scales the RBF such that the function value lies between 0 and 1. A Gaussian RBF in two-dimensions is shown in FIG. 1. Substituting the expression for normalized Gaussian RBF in Eq. (2), the mapping function is given as:

$$\vec{F}(\vec{x}) = \frac{\sum_{i=1}^{N} \vec{c_i} \exp\left(-\frac{\|\vec{x} - \vec{x_i}\|^2}{2s_i^2}\right)}{\sum_{i=1}^{N} \exp\left(-\frac{\|\vec{x} - \vec{x_i}\|^2}{2s_i^2}\right)}. \quad (10)$$

Hence, in this embodiment the mapping function is a linear combination of Gaussian functions whose centers are located at the database inputs.

The widths of the Gaussian RBFs, $s_i$, determine the topographical behavior of the interpolating function. If the widths are too large ($s_i \rightarrow \infty$), then the interpolating function has a flat topography. The function attains a constant value equal to the mean of database outputs:

$$\lim_{s_i \to \infty} \vec{F}(\vec{x}) = \frac{\sum_{i=1}^{N} \vec{y_i}}{N}. \quad (11)$$

On the other hand, if the widths are too small, the function topography has multiple "hills" and "valleys".

Thus, for optimal interpolation, the widths of the Gaussian RBFs are chosen such that they are proportional to the Euclidian nearest neighbor distances in the input space. This choice ensures that the input space is populated by basis functions that have some overlap with the nearest neighbors and negligible overlap with the more distant ones. This idea is illustrated below where RBF interpolation is applied to estimate live oil properties from NMR measurements.

The physical understanding of RBF interpolation can be obtained by considering the special case in which there is negligible overlap between Gaussian RBFs. Let us rewrite the interpolation equations, Eq. (1), in terms of the mapping function as follows:

$$\vec{F}(\vec{x}_j) = \frac{\vec{c}_j + \sum_{\substack{i=1 \\ i \neq j}}^{N} \vec{c}_i \exp\left(-\frac{\|\vec{x}_j - \vec{x}_i\|^2}{2s_i^2}\right)}{1 + \sum_{\substack{i=1 \\ i \neq j}}^{N} \exp\left(-\frac{\|\vec{x}_j - \vec{x}_i\|^2}{2s_i^2}\right)}. \quad (12)$$

If the overlap between RBFs is neglected, the summation in Eq. (12) reduces to:

$$\vec{F}(\vec{x}_j) = \vec{y}_j = \vec{c}_j \quad (13)$$

Substituting Eq. (13) in Eq. (10), results in the mapping function:

$$\vec{F}(\vec{x}) = \frac{\sum_{i=1}^{N} \vec{y}_i \exp\left(-\frac{\|\vec{x} - \vec{x}_i\|^2}{2s_i^2}\right)}{\sum_{i=1}^{N} \exp\left(-\frac{\|\vec{x} - \vec{x}_i\|^2}{2s_i^2}\right)}. \quad (14)$$

Thus, the interpolating function at $\vec{x}$ is the weighted average of the database outputs such that the weights show Gaussian dependence on the proximity of $\vec{x}$ with database inputs. The localized nature of Gaussian functions implies that the mapping function has the largest contribution from the database inputs that are nearest to $\vec{x}$. The database inputs that are far removed from $\vec{x}$ make a negligible contribution to the function.

A database comprising NMR measurements and PVT properties of live oils at elevated temperature and pressure conditions can be constructed. The database is used to estimate PVT properties of live oils not included in the database using the interpolation technique. Before measurements are performed, each live oil sample is equilibrated for one to five days in a pressure cell at a known gas-oil ratio (GOR).

Figure 2:
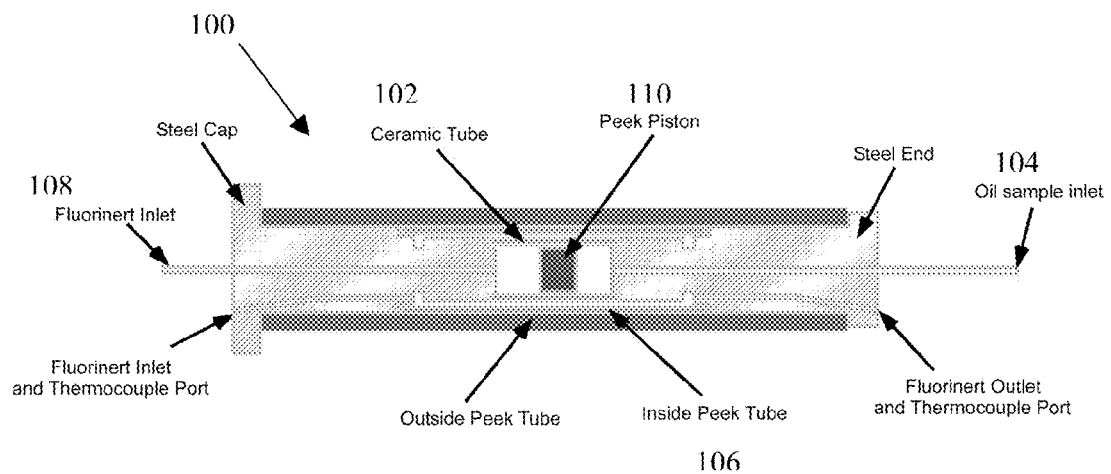
FIG. 2 is a schematic of a pressure cell in which temperature and pressure can be maintained above the bubble point of live oils, according to one or more aspects of the present disclosure.

Acquisition of a database of NMR measurements with live oils was performed using a 2 MHz NMR spectrometer. A pressure cell 100 (FIG. 2), rated to maximum operating conditions of 10,000 psi and 110° C., was installed for high pressure and high temperature measurements. Live oil was charged into the ceramic tube 102 of the sample holder through the ceramic inlet tube 104. The temperature inside the holder was maintained by circulating a fluid such as FLOURINERT coolant through a gap between the ceramic tube 102 and tubes 106 made, for example, of PEEK material, as shown in FIG. 2. A second inlet 108 for the circulating fluid maintains the pressure through the displacement of a piston 110 made, for example, of PEEK material.

Figure 3:
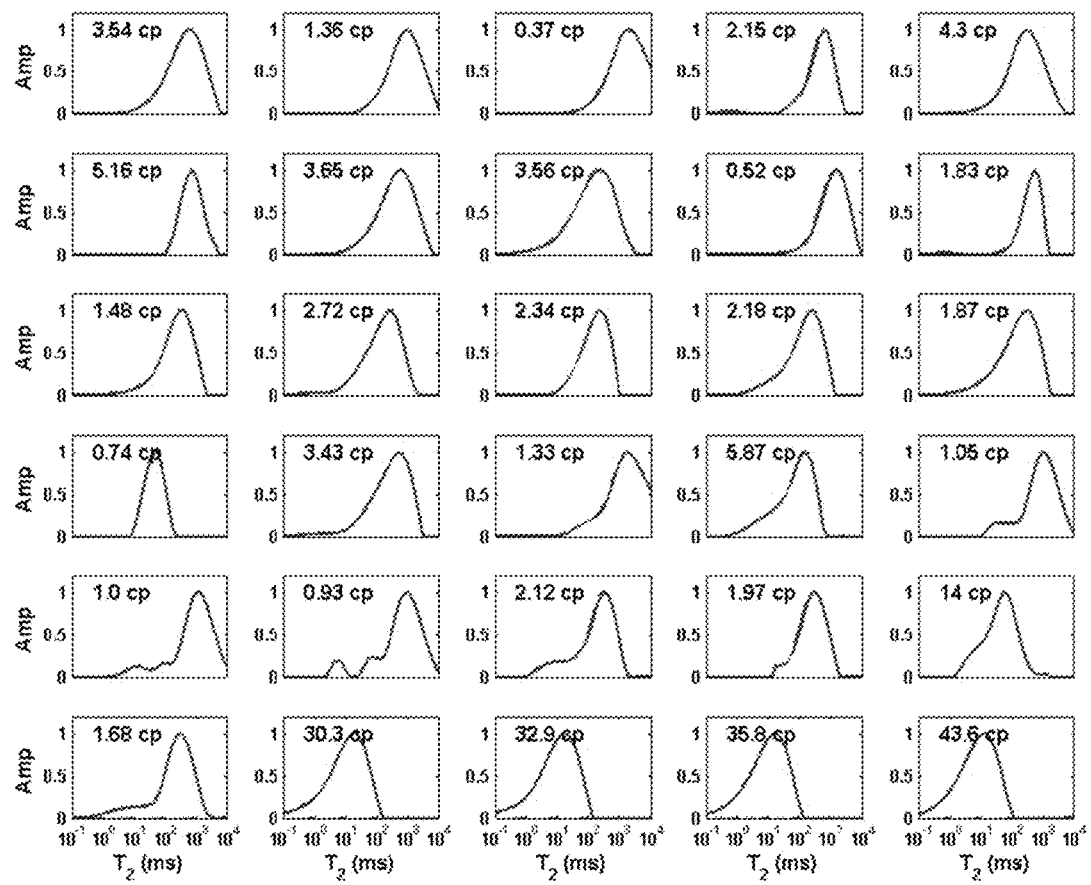
FIG. 3 is a set of plots showing the $T_2$ distributions of 30 live oil samples, according to one or more aspects of the present disclosure. The viscosities of the samples at corresponding temperature and pressure are also shown.
Figure 4:
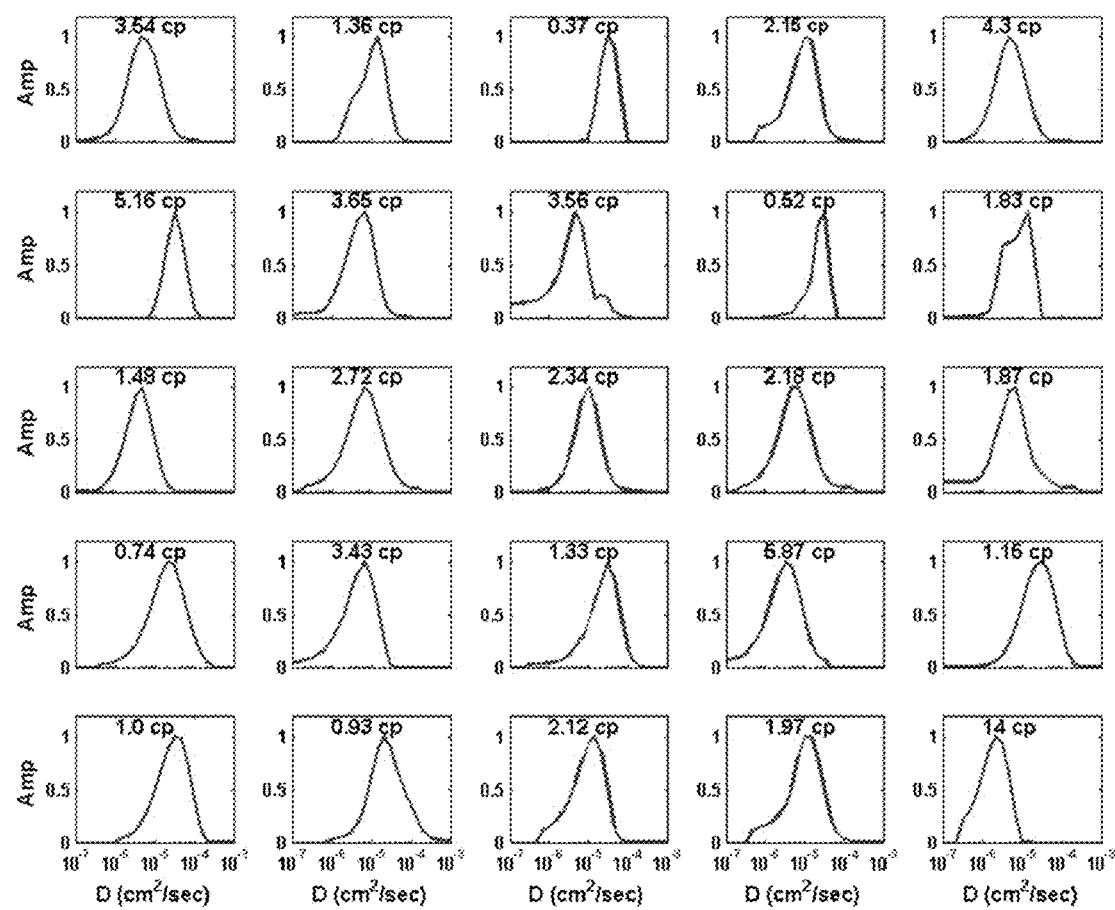
FIG. 4 is a set of plots showing the diffusion distributions of 25 live oil samples, according to one or more aspects of the present disclosure. The viscosities of the samples at corresponding temperature and pressure are also shown.

Three types of NMR measurements were performed to obtain $T_1$ (longitudinal relaxation), $T_2$ (transverse relaxation), and D (diffusivity) distributions of live oils. $T_1$ distributions were measured using a saturation recovery pulse sequence. In most cases, joint probability distributions of $T_1$ and $T_2$ were obtained by two-dimensional measurements in which CPMG sequences were preceded by polarization periods with varying wait times. Ten logarithmically spaced wait times were used to measure the $T_1$ relaxation after saturating the spins with several 90° pulses. $T_2$ distributions were also obtained using a CPMG pulse sequence with a minimal echo spacing of 0.3 ms and a four-step phase cycling. The $T_2$ values were free of diffusion because the spectrometer had no background gradient. FIG. 3 shows the normalized $T_2$ distributions of 30 live oil samples in the database. Diffusivity distributions of live oils were obtained using a pulsed field gradient pulse sequence. FIG. 4 shows the diffusivity distributions of 25 of the live oil samples in the database.

The PVT measurements with live oils include measurements of viscosity, molecular composition, and SARA (saturates, aromatics, resins, asphaltenes) composition. A brief description of the measurements is included below.

An electromagnetic (EM) viscometer was used to measure viscosity of live oils at elevated temperatures and pressures. The viscosity measurement by an EM viscometer is based on the following principle. A magnetic force is applied to a piston which is immersed in the fluid. The viscous damping force of the fluid on the piston is used to derive an accurate fluid viscosity. Table 2 shows the viscosity and GOR of 30 live oil samples in the database.

TABLE 2

Viscosities and GORs of 30 Live Crude Oils

| Sample | Temp (K.) | Pressure (psia) | GOR (ft³/STB) | Measured Viscosity (cp) |
|---|---|---|---|---|
| 1 | 359 | 5962 | 275 | 3.54 |
| 2 | 353 | 8006 | 381 | 1.36 |
| 3 | 354 | 6040 | 885 | 0.37 |
| 4 | 354 | 8027 | 339 | 2.16 |
| 5 | 353 | 6050 | 232 | 4.30 |
| 6 | 353 | 8048 | 759 | 5.16 |
| 7 | 359 | 5564 | 275 | 3.66 |
| 8 | 355 | 8045 | 502 | 3.57 |
| 9 | 366 | 4893 | 628 | 0.52 |
| 10 | 351 | 7891 | 228.6 | 1.84 |
| 11 | 350 | 7877 | 83.17 | 1.48 |
| 12 | 353 | 10070 | 598 | 2.72 |
| 13 | 372 | 7943 | 271 | 2.34 |
| 14 | 351 | 9739 | 563 | 2.18 |
| 15 | 356 | 9562 | 742 | 1.87 |
| 16 | 351 | 10000 | 1026 | 0.74 |
| 17 | 355 | 7994 | 336 | 3.43 |
| 18 | 355 | 8000 | 186.31 | 1.34 |
| 19 | 356 | 9600 | 467.11 | 5.87 |
| 20 | 362 | 7500 | 763.52 | 1.15 |
| 21 | 362 | 5800 | 763.52 | 1.0 |
| 22 | 359 | 4900 | 763.52 | 0.93 |
| 23 | 322 | 7800 | 763.52 | 2.12 |
| 24 | 323 | 7000 | 763.52 | 1.97 |
| 25 | 330 | 5038 | 161.58 | 14.0 |
| 26 | 328 | 5000 | 763.52 | 1.68 |
| 27 | 343 | 1700 | 21.3 | 30.3 |
| 28 | 343 | 2350 | 21.3 | 32.9 |
| 29 | 343 | 3000 | 21.3 | 35.8 |
| 30 | 343 | 1400 | 11.4 | 43.6 |

Figure 5:
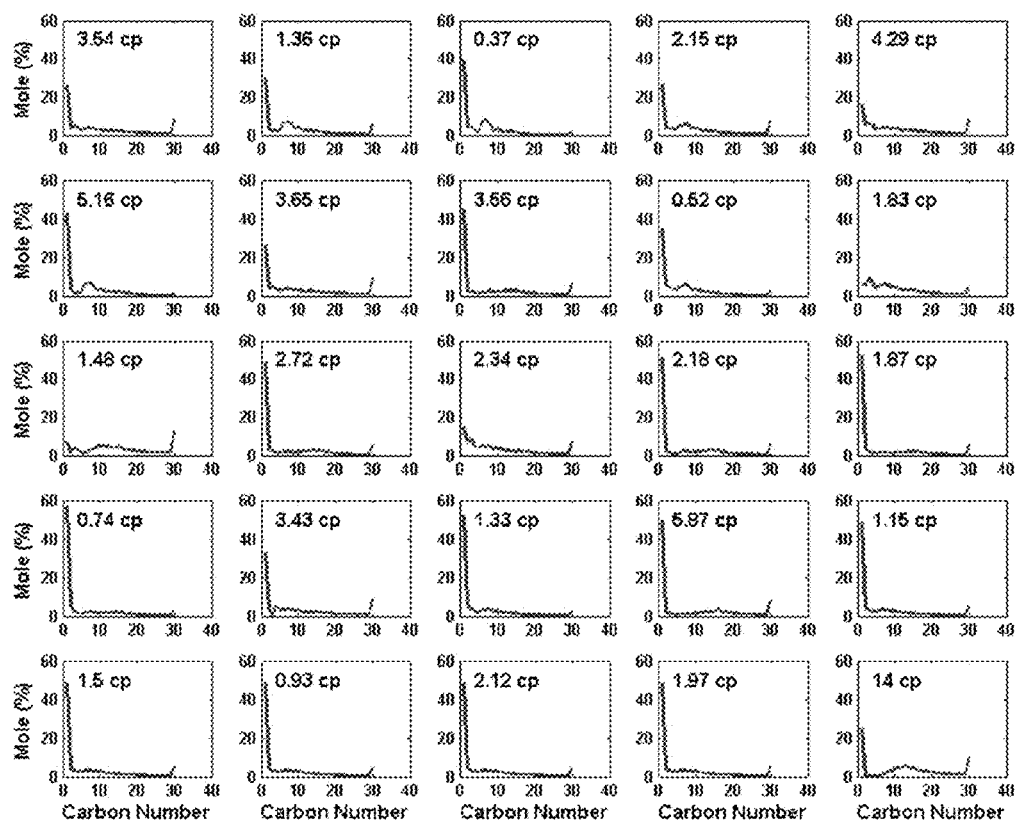
FIG. 5 is a set of plots showing the molecular composition of 25 live oils measured by gas chromatography, according to one or more aspects of the present disclosure. The viscosities of the samples are also shown.

The molecular composition of live oils in the database was analyzed using gas chromatography (GC). The molar fraction of components with carbon numbers ranging from one to 30 and higher was obtained by elutriating the fractions with an inert gas. FIG. 5 shows the molar compositions and corresponding viscosities of 25 oils in the database. The GC data were not available for the remaining five oils.

The SARA compositions of crude oils were obtained using a standard ASTM technique. The live oil sample was flashed in an inert nitrogen environment to remove all volatiles from the oil. The flashed oil was separated into asphaltene and maltene fractions by precipitating asphaltenes with an excess of hot heptane. The maltene fractions were further separated into saturates, aromatics, and resins by selective elutriation on activated alumina columns. Saturates were elutriated using n-heptane, aromatics using toluene, and resins using equal volumes of dichloromethane and methanol. The masses of each fraction were carefully measured after evaporating the solvent over a hot plate in an inert $N_2$ atmosphere. A combined SARA estimate expressed as a percentage was obtained from the weights of the fractions. A quality check was done, ensuring the error in the yield was within 3%.

The application of the RBF interpolation technique to estimate live oil properties using the laboratory database does not require construction of a physical model, and assumes that the underlying physical relationships between the NMR measurements and the PVT properties are contained in the database.

NMR relaxation in fluids is sensitive to fluid viscosity due to the dependence of rotational and translational correlation times on the viscosity. The phenomenological BPP theory postulates that in the extreme narrowing limit, the relaxation rate of a pure fluid is proportional to the ratio of fluid viscosity ($\eta$) and temperature (T) as shown below:

$$\frac{1}{T_1} = \frac{1}{T_2} \propto \frac{\eta}{T}. \quad (15)$$

The BPP theory assumes that the most significant relaxation mechanism is the intramolecular dipole interactions between hydrogen nuclei. However, this assumption is not valid for live crude oils because methane molecules relax by different mechanisms than larger chain-length hydrocarbons. A mixing rule has been previously developed that correlates the viscosity of mixtures of methane and higher alkanes to the relaxation time, temperature, and gas-oil ratio. This mixing rule assumes that higher alkanes in the mixture relax by intramolecular dipole interaction, while methane relaxes by spin rotation and intermolecular interaction. The relationship is given as:

$$\eta = \frac{aT}{T_{2,LM} f(GOR)}, \quad (16)$$

where $T_{2,LM}$ is the logarithmic mean of the $T_2$ distribution and f(GOR) is an empirically determined function of gas-oil ratio. The parameters for the empirical relationship were obtained from $T_2$ and viscosity measurements with several methane-alkane mixtures. Eq. (16) is frequently employed for estimation of viscosity of live crude oils. However, the accuracy of the estimates is limited for several reasons. First, the viscosity estimates in Eq. (16) depend only on the logarithmic mean of the $T_2$ distribution, i.e., the shape of the distributions are not taken into account. Second, the effect of pressure on the viscosity of the oils is not explicitly incorporated into the model. Third, the empirical constant a needs to be calibrated for different crude oil samples, and the variance in the value can cause significant errors in the estimates. Last, the mixing rule is derived for mixtures of linear alkanes and hence, the proposed relationship may not be valid if non-linear components are present in the crude oil.

RBF interpolation is an ideal technique for estimating viscosity of complex systems such as crude oils from relaxation times or diffusivity distributions. The technique is independent of a physical or empirical model, and incorporates the shape of the distribution into the estimation. Using Eq. (10), viscosity can be expressed as a linear combination of Gaussian RBFs whose arguments depend on the amplitudes of the $T_2$ or D distribution, temperature, pressure, and GOR, as shown below:

$$\eta = \frac{\sum_{i=1}^{N} c_i \exp\left(-\frac{\|\vec{A}_T - \vec{A}_{T,i}\|^2}{2s_i^2}\right)}{\sum_{i=1}^{N} \exp\left(-\frac{\|\vec{A}_T - \vec{A}_{T,i}\|^2}{2s_i^2}\right)}. \quad (17)$$

Here $\vec{A}_T$ is a vector containing the amplitudes of a $T_2$ distribution, $A(T_2)$, and/or a diffusivity distribution, $A(D)$, as well as temperature, pressure, and GOR of a live oil sample:

$$\vec{A}_T = \vec{A}_T(A(T_2), A(D), T, P, GOR) \quad (18)$$

The amplitudes of the $T_2$ or D distributions are normalized with the largest respective values to eliminate the dependence on hardware or software settings. Raw echo values, window sums of echoes, or moments of echoes can also be used instead of the amplitudes of $T_2$ or D distributions since those data sets contain the same information. Window sums are obtained by summing the echoes in pre-defined bins. Moments of echoes can be obtained by projecting the echoes onto basis vectors obtained from a singular value decomposition of the NMR measurement matrix. In addition, the values of temperature, pressure, and GOR in the input vector are also made dimensionless by normalizing with their respective largest value in the database. The coefficients c are determined from the solution of interpolation equations, given by Eq. (4). The matrices $\Phi$ and Y are obtained using the database of NMR and viscosity measurements with a representative suite of live oils. Specifically, $$\Phi_{i,j} = \frac{\exp\left(-\frac{\|\vec{A}_{T,i} - \vec{A}_{T,j}\|^2}{2s_j^2}\right)}{\sum_{j=1}^{N} \exp\left(-\frac{\|\vec{A}_{T,i} - \vec{A}_{T,j}\|^2}{2s_j^2}\right)} \quad 1 \leq i, j \leq N, \quad (19)$$

$$y_i = \eta_i. \quad (20)$$

$\vec{A}_T$ is given by Eq. (18), and N is the number of live oil samples in the database. The viscosity of a live oil not contained in the database can be estimated from Eq. (17) using the measured inputs for this sample.

Figure 6:
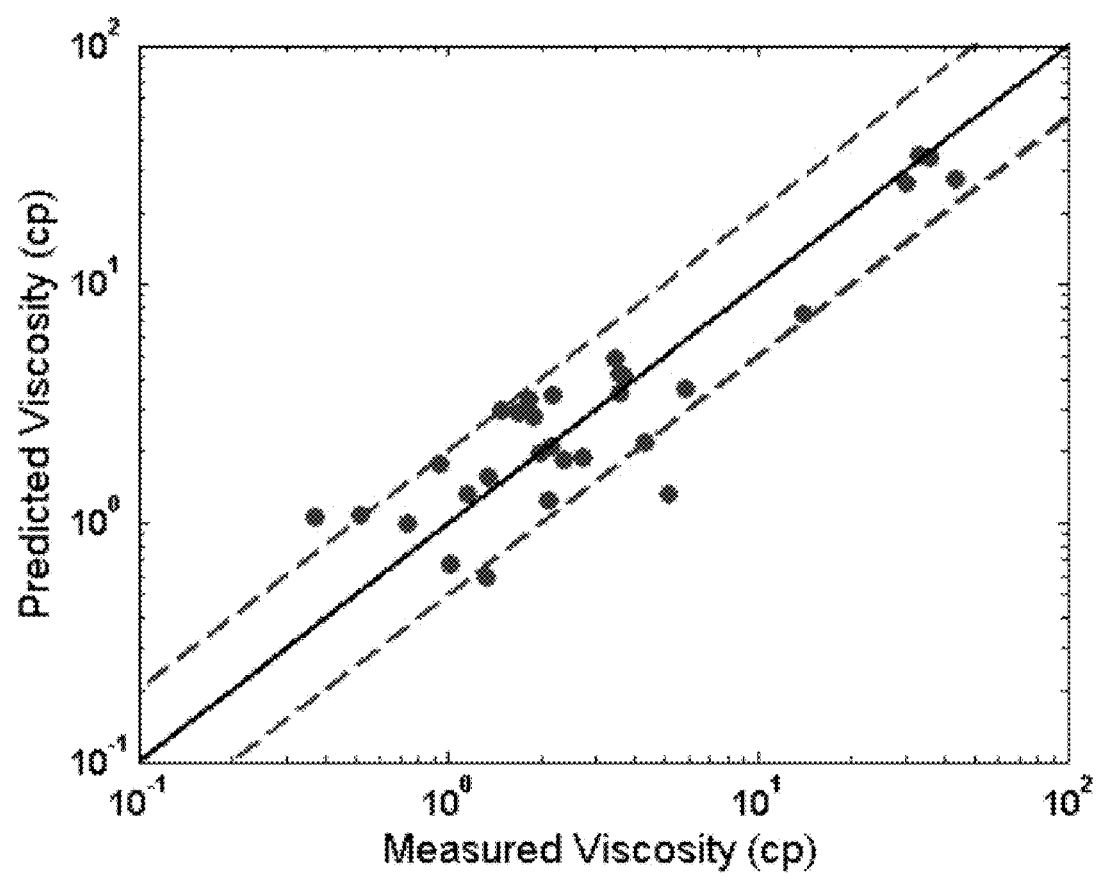
FIG. 6 is a plot comparing live-oil viscosities estimated from $T_2$ distributions using the interpolation technique with values measured in the laboratory, according to one or more aspects of the present disclosure. The solid black line is the best-fit line and the dashed lines are located at a deviation factor of two.

Thus, the interpolation technique can be used to estimate viscosities of live oils using the laboratory database. FIG. 6 shows a comparison of live oil viscosities estimated from Eq. (17) with values measured in laboratory. The estimates were obtained using the "leave-one out" method, whereby each live oil sample was removed from the database and its viscosity was estimated from the interpolating function obtained using the remaining samples. The input vector for each live oil comprised normalized amplitudes of $T_2$ distribution and normalized temperature, pressure, and GOR. To ensure sufficient overlap between RBFs, the widths $s_j$ were chosen to be proportional to the Euclidian nearest-neighbor (NN) distances as shown in the following equation:

$$s_j = \alpha(NN)_j \quad (21)$$

Table 3 lists the NN distances in the input space. The proportionality constant, $\alpha$, was determined by minimizing the deviation between measured and estimated viscosities. In this case, the optimal $\alpha$ was 0.5. The viscosities were predicted within less than a factor of two for most oils over the entire range.

TABLE 3

Nearest neighbor distances of 30 live oil samples

| Sample | Viscosity | NN Distances |
|---|---|---|
| 1 | 3.54 | 0.1013 |
| 2 | 1.36 | 0.6438 |
| 3 | 0.37 | 0.7384 |
| 4 | 2.157 | 0.5332 |
| 5 | 4.299 | 0.5262 |
| 6 | 5.16 | 0.7917 |
| 7 | 3.66 | 0.1013 |
| 8 | 3.57 | 0.4951 |
| 9 | 0.52 | 0.4303 |
| 10 | 1.84 | 0.5332 |
| 11 | 1.48 | 0.5262 |
| 12 | 2.72 | 0.2921 |
| 13 | 2.34 | 0.5489 |
| 14 | 2.18 | 0.3831 |
| 15 | 1.873 | 0.2921 |
| 16 | 0.74 | 1.3623 |
| 17 | 3.43 | 0.5498 |
| 18 | 1.34 | 0.7384 |
| 19 | 5.87 | 1.1129 |
| 20 | 1.15 | 0.3668 |
| 21 | 1.0 | 0.3668 |
| 22 | 0.93 | 0.5068 |
| 23 | 2.12 | 0.4033 |
| 24 | 1.97 | 0.4559 |
| 25 | 14 | 1.3445 |
| 26 | 1.68 | 0.4033 |
| 27 | 30.3 | 0.1940 |
| 28 | 32.9 | 0.1805 |
| 29 | 35.8 | 0.1805 |
| 30 | 43.6 | 0.3516 |

Figure 7:
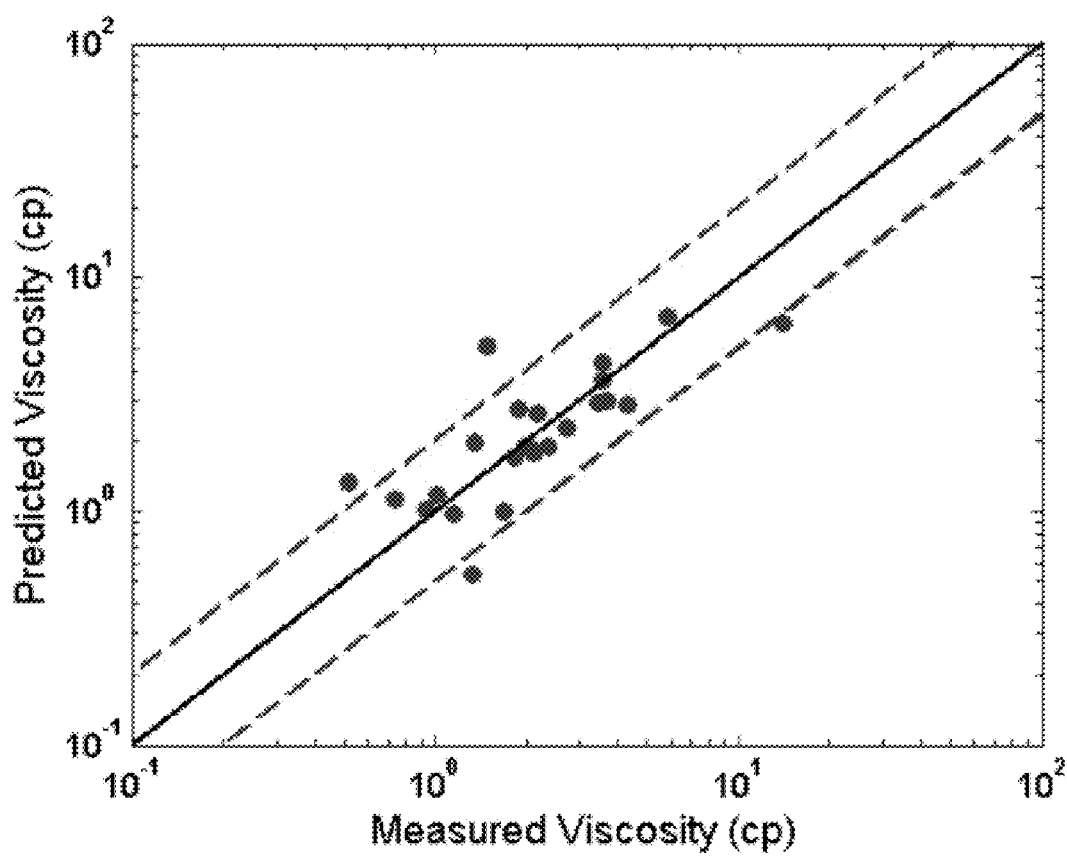
FIG. 7 is a plot comparing live-oil viscosities estimated from diffusivity distributions using the interpolation technique with values measured in the laboratory, according to one or more aspects of the present disclosure. The solid black line is the best-fit line and the dashed lines are located at a deviation factor of two.

Viscosities can also be estimated using the amplitudes of a diffusivity distribution for RBF interpolation. FIG. 7 shows a comparison of viscosities of 25 live oils estimated using Eq. (17) with laboratory-measured values. The input vector included normalized amplitudes of the D distribution, and normalized temperature, pressure, and GOR. The widths of the RBFs were heuristically determined to be 1.2 times the NN distances. Similar to FIG. 6, the viscosities were estimated within less than a factor of two for most cases. No further improvement in the accuracy of the estimates was observed when the amplitudes of the $T_2$ and D distributions were combined in the input vector. This observation is consistent with numerical experiments showing that the accuracy of RBF interpolation is independent of the dimensionality of the database inputs. A final and important conclusion is that sufficient accuracy can be obtained from a relatively small database (e.g., 25 to 30 samples).

It is well known that the diffusivity of a spherical molecule in a dispersion is related to its size. This dependence is clearly elucidated in the Stokes-Einstein relationship:

$$D = \frac{k_B T}{6\pi \eta a_s}, \qquad (22)$$

where $a_s$ is the radius of the diffusing spherical particles, $k_B$ is Boltzmann's constant, T is the temperature, and $\eta$ is the viscosity of the solvent. Eq. (22) is strictly valid only for hard spheres at dilute concentrations such that the interactions between the spheres and the resulting effect on viscosity can be neglected. Similarly, the relaxation time of a molecule is related to its size. Smaller molecules generally have longer relaxation times. Thus, the molecular composition of a mixture can be estimated from $T_2$ or D distributions if the interactions between different components can be theoretically modeled.

For molecules with internal degrees of freedom, e.g., polymer melts, diffusivity is still related to the size of the molecule; however, Eq. (22) is no longer applicable. In linear polymers, diffusivity is found to scale inversely with the number of segments, $N_s$, as shown below:

$$D \propto N_S^{-\kappa} \qquad (23)$$

The exponent $\kappa$ ranges from ½ to two, depending on whether the hydrodynamic interactions are significant and on entanglement of polymeric chains. It has been postulated that in a mixture of linear n-alkanes, the diffusivity of a component scales with the chain length as shown below:

$$D_i = N_{s,i}^{-\nu} g \qquad (24)$$

The term g is dependent on bulk properties such as viscosity and composition. A similar scaling law between $T_2$ and chain length has also been proposed. A physical model was applied to accurately estimate the chain length distribution of dead crude oil samples that had high concentration of paraffins. At least one other model for estimating the composition of crude oil has been proposed. However, the accuracy of compositions predicted by such physical models is limited because the underlying assumptions made in deriving the models may not be valid for real crude oils. For example, one such model assumes that the crude oil is a mixture of linear alkanes. The presence of components other than linear alkanes such as branched hydrocarbons, aromatics, and asphaltenes can significantly influence the accuracy of the physical model.

The interpolation technique, however, can be easily applied for estimating molecular compositions from $T_2$ or D distributions. The multivariate function of Eq. (10) maps the database inputs to compositions $\vec{C}_m$ such that the coefficients c are vector quantities of same dimensions as the compositions. Mathematically, $$\vec{C}_m = \frac{\sum_{i=1}^{N} \vec{c}_i \exp\left(-\frac{\|\vec{A}_T - \vec{A}_{T,i}\|^2}{2s_i^2}\right)}{\sum_{i=1}^{N} \exp\left(-\frac{\|\vec{A}_T - \vec{A}_{T,i}\|^2}{2s_i^2}\right)}. \qquad (25)$$

The input vector $A_T$ comprises amplitudes of $T_2$ or D distributions, temperature, pressure, and GOR. Similar to the estimation of viscosity, the amplitudes of $T_2$ or D distribution, temperature, pressure and GOR are normalized with appropriate factors.

Figure 8:
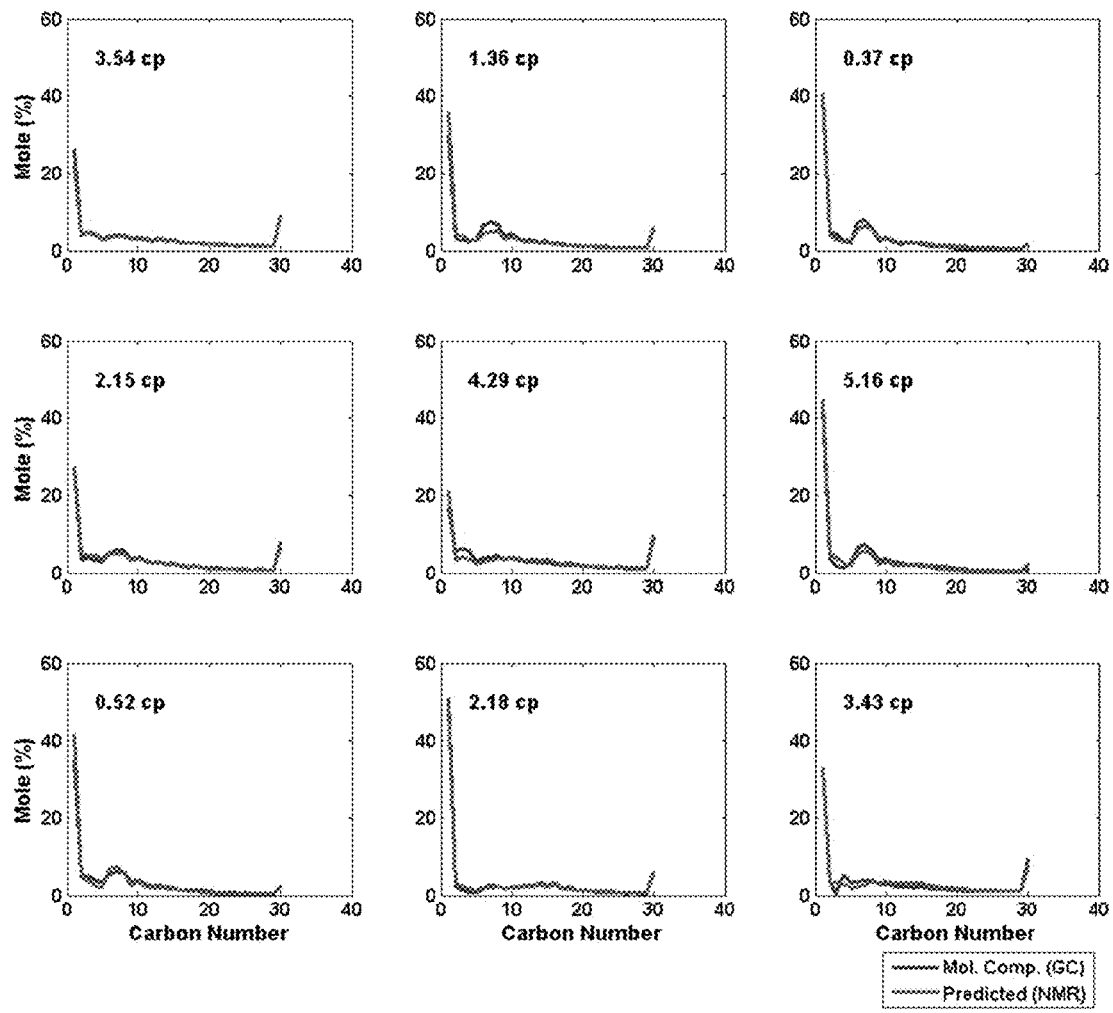
FIG. 8 is a set of plots comparing the molecular compositions of nine live oils estimated from D distributions using the interpolation technique with those measured in the lab using gas chromatography, according to one or more aspects of the present disclosure.

The estimation of composition from Eq. (25) was tested on the database of 25 live oils shown in FIG. 5. The molecular composition of those oils was measured in the laboratory using GC. A comparison of the estimated compositions with the measured values is shown in FIG. 8. For clarity, the comparison is shown for nine live oils in the database. Compositions were estimated from Eq. (25) using amplitudes of D distributions and normalized temperature, pressure, and GOR as inputs. The widths of the RBFs were heuristically determined such that $\alpha$ in Eq. (21) was equal to one, although the estimates were relatively insensitive to values of $\alpha$ ranging from 0.2 to one. The compositions were estimated using the "leave-one out method". An excellent correlation between measured and estimated compositions is observed for most oils in the database.

Figure 9:
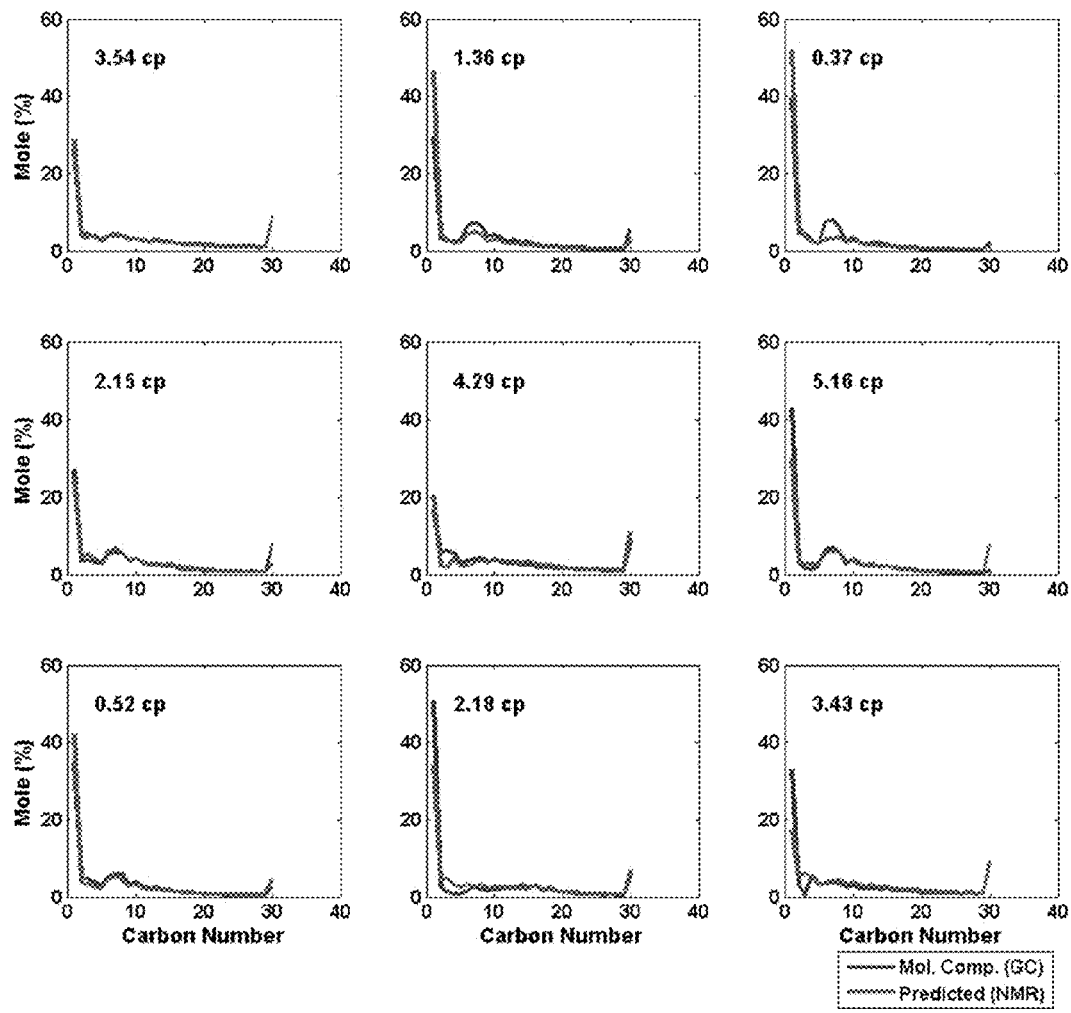
FIG. 9 is a set of plots comparing the molecular compositions of nine live oils estimated from $T_2$ distributions using the interpolation technique with those measured in the lab using gas chromatography, according to one or more aspects of the present disclosure.

FIG. 9 shows the compositions predicted using amplitudes of $T_2$ distributions, temperature, pressure, and GOR as inputs for RBF interpolation. The widths were heuristically determined such that $\alpha$ in Eq. (21) was equal to 0.8. Once again, an excellent agreement between estimated and measured compositions is observed. The result that nearly identical compositions are estimated from either D or $T_2$ distributions is consistent with the knowledge that essentially the same information is contained in both distributions.

The estimation of the saturates, aromatics, resins, and asphaltenes (SARA) content of crude oils is important for fluid characterization. SARA analysis helps to provide a consistent basis for comparing oil samples by characterizing the sample according to polarizability. SARA fractions are also used to devise flow assurance strategies for prevention of asphaltene deposition and to assess the economics of a potential field development with less uncertainty.

NMR relaxation provides an excellent probe for analyzing the different species present in a crude oil. For example, it has been found that for heavy oils, the $T_1/T_2$ ratio correlates to the asphaltene content. It has been shown that the diffusivity of oils with more than 1% asphaltene content deviates from the established alkane correlation with $T_2$ relaxation time. This deviation was explained to arise from the shortening of crude oil relaxation time in the presence of asphaltenes due to hindered rotational motion of maltene molecules. Additionally, it has been found that the slope of the distributions in the D-$T_2$ domain correlates to the asphaltene content. However, the results obtained remain qualitative.

A quantitative estimate of the SARA content of oils can be obtained from NMR measurements using RBF interpolation. Analogous to the estimation of molecular composition, the SARA content of the oils can be estimated from Eq. (10) such that the coefficients $c_j$ are four dimensional vectors:

$$\overrightarrow{SARA} = \frac{\sum_{i=1}^{N} \vec{c}_i \exp\left(-\frac{\|\vec{A}_T - \vec{A}_{T,i}\|^2}{2s_i^2}\right)}{\sum_{i=1}^{N} \exp\left(-\frac{\|\vec{A}_T - \vec{A}_{T,i}\|^2}{2s_i^2}\right)}. \quad (26)$$

Figure 10:
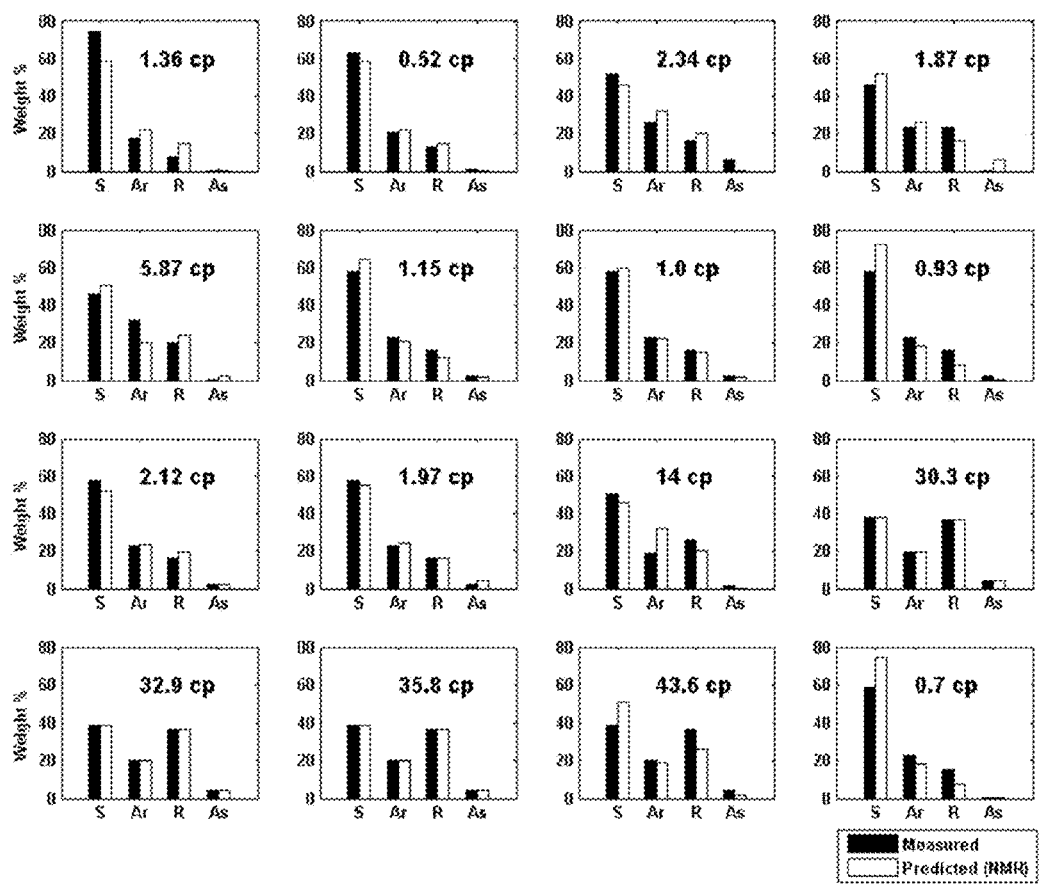
FIG. 10 is a set of plots comparing the SARA fractions of live oils predicted from RBF interpolation with values measured in the laboratory, according to one or more aspects of the present disclosure.

The values estimated from Eq. 26 were compared to laboratory-measured values, as shown in FIG. 10. The input vector, $\vec{A}_T$, includes normalized amplitudes of a $T_2$ distribution, and normalized temperature, pressure, and GOR. The widths were determined such that α in Eq. (21) was equal to 0.25. The SARA components were estimated within a 13% average absolute deviation.

RBF interpolation develops a continuous, smooth mapping between database inputs and outputs. As a result, a small variation in the inputs due to uncertainty in measurements or noise in the data leads to only a small variation in the estimation of outputs. This argument can be intuitively understood by recalling that the RBF mapping function at $\vec{x}$ is a weighted average of terms that depend on the Euclidean distances of $\vec{x}$ from database inputs. Small errors in measurement of $\vec{x}$ result in minor modifications of the distances, thereby leading to a small variation in the estimation of the outputs.

The relative error in estimation due to uncertainty or noise in the measurement of $\vec{x}$ is given by:

$$\left(\frac{\Delta \vec{F}}{\vec{F}}\right) \leq k \sqrt{\sum_{j=1}^{n} (\Delta x^j)^2}. \quad (27)$$

Figure 11:
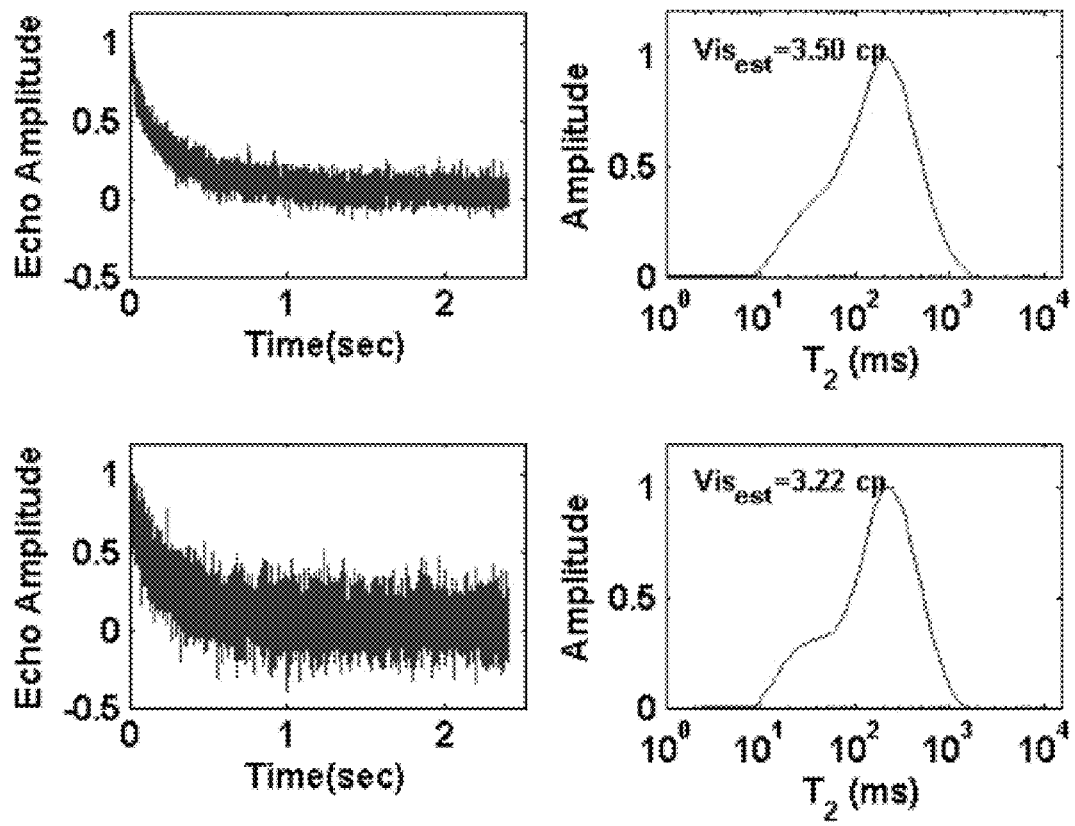
FIG. 11 is a set of plots showing the effect of noise in the estimation of viscosity using RBF interpolation, according to one or more aspects of the present disclosure. The upper panel shows the raw data and the corresponding $T_2$ distribution. The lower panel shows the data and $T_2$ distribution with twice the noise.

In the above equation $\Delta \vec{F}$ is the error in the estimation of $\vec{F}$, $\Delta x^j$ is the variance in the measurement of the jth dimension of $\vec{x} \in \mathbb{R}^n$, and k is a constant. This equation shows that the relative error in $\vec{F}$ due to noise is constrained by the variance in $\vec{x}$. However, in the upper limit of the error in Eq. (27) is a conservative estimate, and in general, the error is much less. This estimation error due to noise is best illustrated by numerical analysis of the variance in the output as a function of noise in the input measurement. For the live oil sample 1, $T_2$ distributions at different noise levels were simulated by adding white Gaussian noise to the raw echo data. The resulting distributions were used to estimate the viscosity using the interpolating function of Eq. (17). As is shown in FIG. 11, the estimate of viscosity changes by less than 10% even when the noise in the $T_2$ distribution increases by 100%. The analysis demonstrates that the interpolation technique is robust and relatively insensitive to the measurement noise.

Let us mathematically quantify the effect of measurement noise on RBF interpolation. The variance of a multivariate function $\vec{F}(\vec{x})$, $\vec{x} \in \mathbb{R}^n$ is given by Taylor's expansion as follows $$(\Delta \vec{F})^2 = \sum_{j=1}^{n} \left(\frac{\partial \vec{F}}{\partial x^j}\right)^2 (\Delta x^j)^2, \quad (28)$$

where $x^j$ is the $j^{th}$ dimension of the n dimensional vector and $\Delta x^j$ is the corresponding variance. This expression assumes that the uncertainty in the estimation of $\vec{F}$ arises from noise in the measurement of $\vec{x}$, and that there is little uncertainty in the database measurements. The function $\vec{F}$ is a linear combination of RBFs as shown in Eq. (2). Thus, the relative error in the estimation of $\vec{F}$ due to variance in $x^j$ is given as:

$$\left(\frac{\Delta \vec{F}}{\vec{F}}\right)^2 = \frac{\sum_{j=1}^{n} \left(\sum_{i=1}^{N} c_i \frac{\partial}{\partial x^j} \varphi(\|\vec{x} - \vec{x}_i\|)\right)^2 (\Delta x^j)^2}{\left(\sum_{i=1}^{N} c_i \varphi(\|\vec{x} - \vec{x}_i\|)\right)^2}. \quad (29)$$

For the sake of simplicity, let us consider the case when φ is an un-normalized Gaussian RBF.

$$\varphi(\|\vec{x} - \vec{x}_i\|) = \exp\left(-\frac{\|\vec{x} - \vec{x}_i\|^2}{s_i^2}\right). \quad (30)$$

The derivative of φ with respect of $x^j$ is given as, $$\frac{\partial}{\partial x^j} \varphi(\|\vec{x} - \vec{x}_i\|) = \frac{-2}{s_i^2}(x^j - x_i^j)\varphi(\|\vec{x} - \vec{x}_i\|). \quad (31)$$

Let the minimum nearest neighbor distance between input vectors in the database be s, and let the largest deviation of $\vec{x}$ from database inputs be $\delta x_{max}$, i.e., $$\min(s_j) = s, \quad (32)$$

$$\max(\delta x) = \max_i \left(\sqrt{\sum_{j=1}^{n}(x^j - x_i^j)^2}\right) = \delta x_{max}.$$

From Equations (31) and (32), $$\frac{\partial}{\partial x^j}\varphi(\|\vec{x}-\vec{x}_i\|) \le \frac{2\delta x_{max}}{s}\varphi(\|\vec{x}-\vec{x}_i\|). \quad (33)$$

Substituting Eq. (33) in Eq. (29), we get:

$$\left(\frac{\Delta\vec{F}}{\vec{F}}\right)^2 \le \frac{\sum_{j=1}^{n}\left(\sum_{i=1}^{N}c_i\frac{2\delta x_{max}\varphi(\|\vec{x}-\vec{x}_i\|)}{s}\right)^2}{\left(\sum_{i=1}^{N}c_j\varphi(\|\vec{x}-\vec{x}_i\|)\right)^2}(\Delta x^j)^2, \quad (34)$$

$$\Rightarrow \left(\frac{\Delta\vec{F}}{\vec{F}}\right) \le \frac{2\delta x_{max}}{s}\sqrt{\sum_{j=1}^{n}(\Delta x^j)^2},$$

$$\left(\frac{\Delta\vec{F}}{\vec{F}}\right) \le k\sqrt{\sum_{j=1}^{n}(\Delta x^j)^2}, k = \frac{2\delta x_{max}}{s}.$$

The above disclosure teaches a new approach for quantitative estimation of live oil properties from NMR measurements. The proposed estimation technique assumes there exists a deterministic and unique relationship between NMR response and crude oil properties. This relationship, although not known in closed functional form, is sufficiently contained in a database of NMR and PVT measurements of a suite of live oils. The relationship can be approximated by a multivariate function that maps NMR measurements to PVT properties. The mapping function is preferably a linear combination of Gaussian radial basis functions (RBFs). The coefficients of the mapping function are determined uniquely from the database measurements such that the function is exactly satisfied for each live oil sample in the database. For a live oil sample that is not included in the database, an estimate of the PVT property can be obtained from NMR measurements using the mapping function with calibrated coefficients. Such an estimate is thus consistent with the database measurements. If the database is sufficiently populated with representative live oil samples, accurate estimates can be obtained.

The physical models that relate NMR measurements to crude oil properties have limited accuracy due to inherent complexity of crude oil systems. A model-independent technique is proposed for estimating properties of live crude oils from NMR measurements. The proposed method assumes that the underlying physical relationship between NMR response and crude oil properties is contained in a database of measurements. This relationship is approximated by a mapping function that is a linear combination of Gaussian radial basis functions. The coefficients of the mapping function are determined such that the function is exactly satisfied for each live oil sample in the database. The mathematical properties of Gaussian RBFs ensure that a unique solution exists for function coefficients. For a sample not contained in the database, the desired fluid property can be obtained from the mapping function. The technique is capable for providing accurate estimates if the database is populated with representative samples. Application of the estimation technique shows that accurate estimates of viscosities, molecular compositions and SARA fractions of live oils can be obtained from NMR measurement. A small database of relatively few samples is required to obtain sufficient accuracy. Numerical analysis shows that the technique is robust and relatively insensitive to measurement noise. The model-independent technique is applicable for solving inverse problems for complex systems for which a simple forward model cannot be formulated.

An extensive database of NMR and PVT measurements made on live oils was used to validate the technique. The database was acquired using a 2 MHz NMR spectrometer and a pressure cell for performing measurements on live oils at elevated temperatures and pressures. Viscosities, molecular compositions, and SARA fractions of live oils were determined accurately from NMR measurements using the interpolation technique. The technique can be implemented for downhole characterization of live oils at in-situ temperature and pressure conditions.

Figure 12:
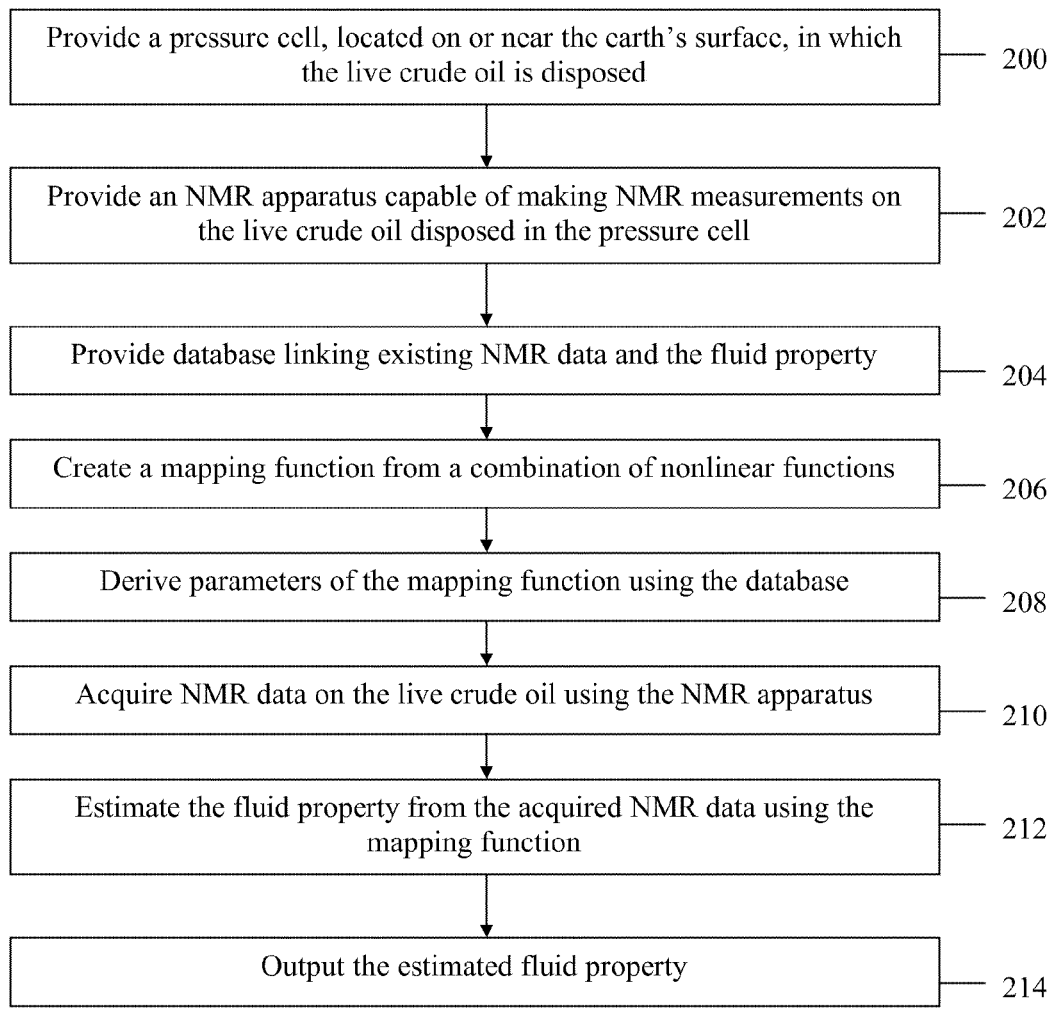
FIG. 12 is a flow-chart diagram of at least a portion of a method, according to one or more aspects of the present disclosure.

Estimates of fluid properties can be obtained as shown in FIG. 12. A pressure cell and an NMR tool are provided (steps 200, 202). A database linking existing NMR measurements to the fluid properties is also provided (step 204). A mapping function is created from a combination of RBFs (step 206) and parameters are derived using the database (step 208). NMR measurements are made to acquire NMR data (step 210). Fluid properties are estimated from the acquired NMR data using the mapping function (step 212) and output to an output device (step 214).

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A method to estimate, using nuclear magnetic resonance (NMR) measurements, a fluid property of live crude oil removed from an earth formation, comprising:
   providing a pressure cell, located on or near the earth's surface, in which the live crude oil is disposed;
   providing an NMR apparatus capable of making NMR measurements on the live crude oil disposed in the pressure cell;
   providing a database linking existing NMR data and the fluid property;
   creating a mapping function from a combination of non-linear functions;
   deriving parameters of the mapping function using the database;
   acquiring NMR data on the live crude oil using the NMR apparatus;
   estimating the fluid property from the acquired NMR data using the mapping function; and
   outputting the estimated fluid property.

2. The method of claim 1, wherein the fluid property includes viscosity, molecular composition, or SARA fractions.

3. The method of claim 1, wherein the acquired NMR data are raw echoes, window sums of raw echoes, moments of raw echoes, T1 distributions, T2 distributions, and/or diffusivity distributions.

4. The method of claim 1, wherein the database is produced from a suite of representative fluids.

5. The method of claim 1, wherein the nonlinear functions are radial basis functions.

6. The method of claim 5, wherein the radial basis functions are Gaussian radial basis functions.

7. The method of claim 5, wherein the radial basis functions are normalized.

8. The method of claim 1, wherein the fluid property is determined independent of a physical model or an empirical model.

9. The method of claim 1, wherein the estimating the fluid property is substantially insensitive to measurement noise.

10. The method of claim 1, wherein the estimating the fluid property comprises evaluating the mapping function at a corresponding input vector.

11. The method of claim 1, wherein creating the mapping function further comprises using an input vector comprising the amplitudes of a normalized NMR distribution, a normalized temperature value, a normalized pressure value, and a normalized gas/oil ratio value.

12. The method of claim 1, wherein the mapping function is a linear combination of Gaussian radial basis functions whose centers are located at input points of the database.

13. The method of claim 12, wherein the Gaussian radial basis functions have widths that are proportional to the Euclidean nearest neighbor distances in an input space.

14. The method of claim 1, further comprising equilibrating the live crude oil in the pressure cell for one or more days.

15. The method of claim 1, further comprising characterizing the live crude oil using the fluid property.

16. The method of claim 15, wherein the live crude oil characterization includes using SARA fractions to devise a flow assurance strategy and/or assess the economics of developing a field of hydrocarbons.

17. A nuclear magnetic resonance (NMR) system to estimate, using nuclear magnetic resonance (NMR) measurements, a fluid property of live crude oil removed from an earth formation, comprising:

a pressure cell, located on or near the earth's surface, in which the live crude oil is disposed;

an NMR apparatus capable of making NMR measurements on the live crude oil disposed in the pressure cell;

an output device; and a processor capable of: (1) storing a database linking existing NMR data and the fluid property; (2) creating a mapping function from a combination of nonlinear functions; (3) deriving parameters of the mapping function using the database; (4) storing NMR data on the live crude oil obtained using the NMR apparatus; (5) estimating the fluid property from the acquired NMR data using the mapping function; and (6) outputting the estimated fluid property to the output device.

18. The NMR system of claim 17, wherein the pressure cell includes a sample chamber enclosed at least partially by one or more conductive materials.

19. The NMR system of claim 17, wherein the NMR apparatus includes an RF antenna either inside or outside a sample chamber in the pressure cell.

20. A nuclear magnetic resonance (NMR) system to estimate, using nuclear magnetic resonance (NMR) measurements, a fluid property of live crude oil removed from an earth formation, including a pressure cell, located on or near the earth's surface, in which the live crude oil is disposed, an NMR apparatus capable of making NMR measurements on the live crude oil disposed in the pressure cell, a database linking existing NMR data and the fluid property, and a computer-readable medium having a set of computer-readable instructions encoded thereon that, when executed, perform acts comprising:

creating a mapping function from a combination of nonlinear functions;

deriving parameters of the mapping function using the database;

acquiring NMR data on the live crude oil using the NMR apparatus;

estimating the fluid property from the acquired NMR data using the mapping function; and outputting the estimated fluid property.

* * * * *